June 5, 1973 R. E. PINKERTON Plant Pat. 3,350
NECTARINE TREE
Filed Oct. 20, 1971
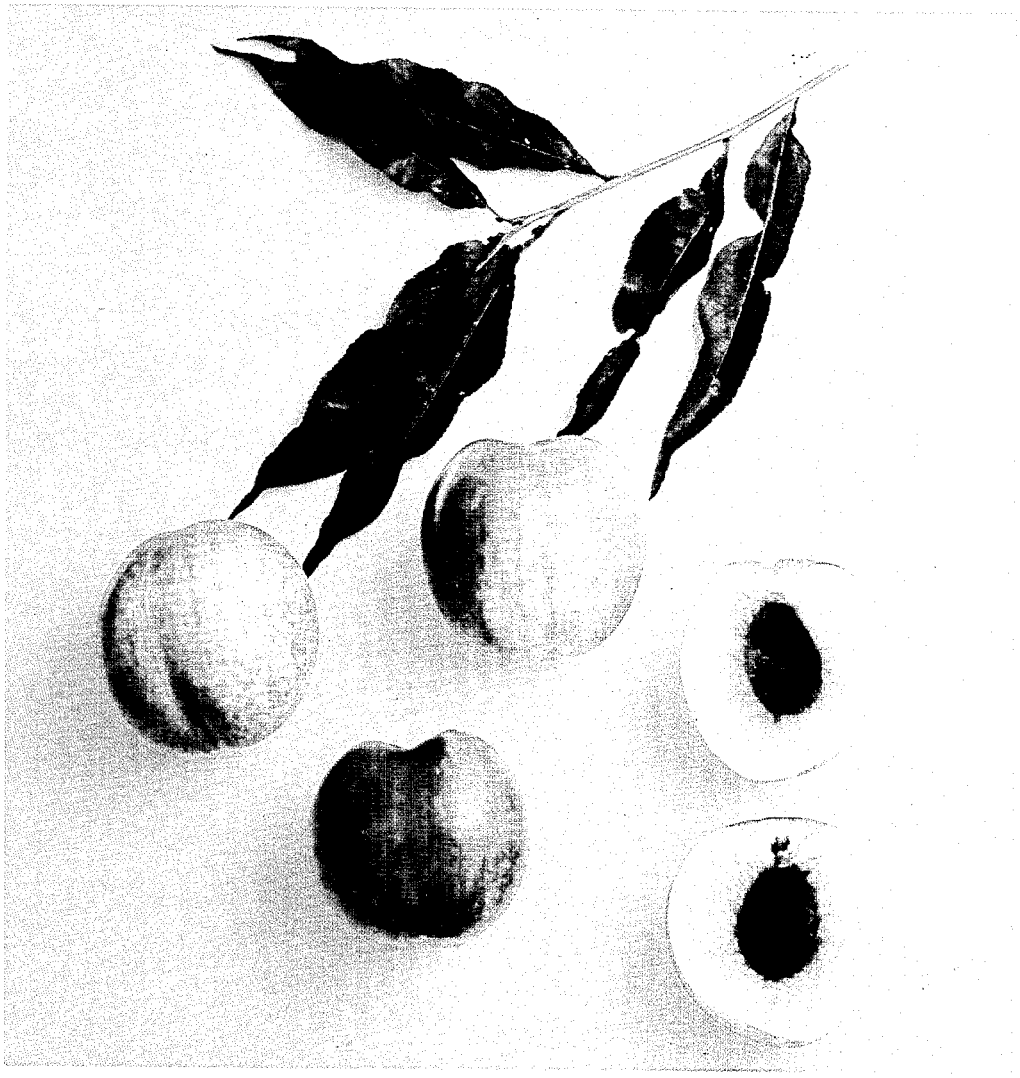

United States Patent Office

Plant Pat. 3,350
Patented June 5, 1973

3,350

NECTARINE TREE

Robert E. Pinkerton, 4445 Avenue 416,
Reedley, Calif. 93654

Filed Oct. 20, 1971, Ser. No. 191,043
Int. Cl. A01h 5/03
U.S. Cl. Plt.—41 1 Claim

ABSTRACT OF THE DISCLOSURE

A large to medium size nectarine tree which is vigorous, upright to spreading, and a regular and productive to very productive bearer of large, uniform, symmetrical, globose, clingstone fruit which ripens about ten days later than the Gold King nectarine (United States Plant Patent No. 1,424); the fruit ripening evenly, being glossy, and having yellow skin substantially overspread with red at maturity, and firm, crisp, meaty, yellow flesh, the surface of the pit cavity being red which streaks into the flesh.

ORIGIN OF THE VARIETY

The present variety of nectarine tree was originated by me on a ranch, of which I am the owner, located near Reedley, Fresno County, Calif. More particularly, seeds of an open-pollinated bud mutation—which bore highly colored fruit and occurred on a Gold King tree in an orchard on the aforesaid ranch—were planted by me, and, of the resulting seedlings, one—upon bearing fruit—evidenced novel characteristics and appeared to have substantial commercial promise. I, therefore, selected such one seedling—and which is the present variety—for asexual reproduction.

ASEXUAL REPRODUCTION OF THE VARIETY

The present variety of nectarine tree was asexually reproduced by me, on my ranch located as aforesaid, by grafting on mature orchard trees, and such reproductions ran true to the original tree in all respects.

SUMMARY OF THE VARIETY

The present variety of nectarine tree is of medium size, vigorous, upright to spreading, and a regular and productive to very productive bearer of large, uniform, symmetrical, globose, clingstone fruit which ripens about ten days later than the Gold King nectarine; the fruit ripening evenly, being glossy, and having yellow skin substantially overspread with red at maturity, and firm, crisp, meaty, yellow flesh, the surface of the pit cavity being red which streaks into the flesh.

While, in comparison to the Gold King nectarine, the fruit of the present variety is somewhat similar in general characteristics, there is an evident distinction in that there is absent the red suture line and which—when present as in the fruit of the Gold King—ripens before the remainder of the fruit. Consequently, the fruit of the present variety—which ripens evenly—has better storage and shipping qualities.

BRIEF DESCRIPTION OF THE DRAWING

The drawing is an illustration, by photographic reproduction in color, of leaves and fruit of the variety; one fruit being cut into halves and the stone remaining in one-half.

DESCRIPTION OF THE VARIETY

The botanical details of this new and distinct variety of nectarine tree—with color definitions (except those in common color terms) referenced to Maerz and Paul Dictionary of Color—are as follows:

Tree:
- *Size.*—Large to medium.
- *Vigor.*—Vigorous.
- *Growth.*—Upright to spreading.
- *Production.*—Productive to very productive.
- *Bearing.*—Regular bearer.

Trunk:
- *Size.*—Medium.
- *Texture.*—Medium.

Branches:
- *Size.*—Stocky.
- *Texture.*—Medium.

Leaves:
- *Size.*—Medium to large, average length—7", average width—3".
- *Form.*—Acutely pointed.
- *Thickness.*—Medium.
- *Texture.*—Smooth.
- *Margin.*—Crenate.
- *Petiole.*—Medium length, medium thickness.
- *Glands.*—Average number—2 to 4, mostly 2, opposite, medium size, reniform, position—usually 2 on petiole and often 2 on blade.
- *Color.*—Top side—Medium green (22–J–7), under side—Lighter green (21–L–5).

Flower buds:
- *Size.*—Large.
- *Length.*—Medium.

Flowers:
- *Blooming period.*—Date of first bloom—Mar. 1, 1971. Date of full bloom—Mar. 15, 1971. Medium, as compared with other varieties.
- *Size.*—Large.

Fruit:
- *Maturity when described.*—Eating ripe—Sept. 13, 1971.
- *Date of first picking.*—Sept. 1, 1971.
- *Date of last picking.*—Sept. 13, 1971.
- *Size.*—Uniform, large, average diameter axially—2⅜", average transversely in suture plane—2⅝".
- *Form.*—Uniform, symmetrical, globose.
- *Suture.*—Distinct, extends from base to beyond apex over entire circumference, marked depression beyond pistil point.
- *Ventral surface.*—Rounded.
- *Lips.*—Equal.
- *Cavity.*—Rounded, average depth—⅜", average breadth—⅝".
- *Base.*—Rounded.
- *Apex.*—Very short.
- *Pistil point.*—Inconspicuous.

Skin:
- *Thickness.*—Medium.
- *Texture.*—Medium.
- *Tendency to crack.*—None noted
- *Down.*—Wanting.
- *Color.*—Yellow (10–L–5) substantially overspread with red (6–L–6) streaked and mottled darker red.

Flesh:
- *Amygdalin.*—Wanting.
- *Juice.*—Moderate.
- *Texture.*—Firm, crisp, meaty.
- *Fibers.*—Few.
- *Ripens.*—Evenly.
- *Flavor.*—Subacid, delicate.

*Eating quality.*—Good to best.
*Color.*—Yellow (9–L–4). Surface of pit cavity—Red (7–J–6); the red being streaked into the flesh.

Stone:
*Types*—Cling.
*Size.*—Medium, average length—1⅜", average breadth—1", average thickness—⅝".
*Form.*—Oblong, obovoid.
*Base.*—Straight.
*Hilum.*—Broad, oblong.
*Surface.*—Regularly furrowed.
*Ridges.*—Jagged.
*Pits.*—Circular.
*Dorsal edge.* Full.
*Tendency to split.*—Slight.
*Color.*—Garnet red (7–H–6).

Use: Market—local and long distance shipping.
Keeping quality.—Good.
Resistance to insects and diseases.—No unusual susceptibilities noted.
Shipping quality.—Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially illustrated and described, which is vigorous upright to spreading, and a regular and productive to very productive bearer of large, uniform, symmetrical, globose, clingstone fruit which ripens about ten days later than the Gold King nectarine; the fruit ripening evenly, being glossy, and having yellow skin substantially overspread with red at maturity, and firm, crisp, meaty, yellow flesh, the surface of the pit caviety being red which streaks into the flesh.

No references cited.

ROBERT E. BAGWILL, Primary Examiner